US008058040B2

(12) United States Patent
Op Den Camp et al.

(10) Patent No.: US 8,058,040 B2
(45) Date of Patent: *Nov. 15, 2011

(54) FERMENTATION OF PENTOSE SUGARS

(75) Inventors: Hubertus Johannes Marie Op Den Camp, Oostrum (NL); Harry Ramanoedj Harhangi, Arnhem (NL); Christiaan Van Der Drift, Malden (NL); Jacobus Thomas Pronk, Schipluiden (NL)

(73) Assignee: C5 Yeast Company B.V., Bergen Op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/580,018

(22) Filed: Oct. 15, 2009

(65) Prior Publication Data
US 2010/0035306 A1 Feb. 11, 2010

Related U.S. Application Data

(63) Continuation of application No. 10/500,872, filed as application No. PCT/NL03/00049 on Jan. 23, 2003, now Pat. No. 7,622,284.

(30) Foreign Application Priority Data

Jan. 23, 2002 (EP) ..................................... 02075266

(51) Int. Cl.
C12P 7/06 (2006.01)
C12N 9/00 (2006.01)
C12N 9/90 (2006.01)
C12N 1/20 (2006.01)
C12N 15/00 (2006.01)
C07H 21/04 (2006.01)

(52) U.S. Cl. ..... 435/161; 435/183; 435/233; 435/252.3; 435/320.1; 536/23.2

(58) Field of Classification Search .......................... None
See application file for complete search history.

(56) References Cited

U.S. PATENT DOCUMENTS

| 5,643,758 A | 7/1997 | Guan et al. |
| 5,858,764 A | 1/1999 | De Hollander |
| 5,935,837 A | 8/1999 | Rasmussen |

FOREIGN PATENT DOCUMENTS

| WO | WO 9624667 | 8/1996 |
| WO | WO 00/61733 | 10/2000 |
| WO | WO2004/099381 | 11/2004 |
| WO | WO2006/009434 | 1/2006 |
| WO | WO2010/074577 | 6/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Database EMBL 'Online!'; Mar. 3, 2000; Op Den Camp, HJM; "*Piromyces* sp. E2 mRNA for xylose isomerase (xylA gene)"; Database accession No. AJ249909.
Database EMBL 'Online!' Mar. 3, 2000; Op Den Camp HJM; *Piromyces* sp. E2 mRNA for D-xylulokinase (xylB gene); Database accession No. AJ249910.
Zaldivar, J et al., "Fuel ethanol production from lignocellulose: A challenge for metabolic engineering and process integration."; *Appl Microbiol Biotechnol*.56:17-34 (2001).
Teunissen. Mj et al., "Production of cellulolytic and xylanolytic enzymes during growth of the anaerobic fungus *Piromyces* • Sp on different substrates"; *J. Gen. Microbiol. 138*:657-1664 (1992).
Chica et al. Curr Opin Biotechnol ( Aug. 2005) 16:378-84.
Witkowski et al. . . . *Biochemistry* (Sep. 1999) 38:11643-50.
Sefternick et al. *J Bacteriol.* (Apr. 2001) 183:2405-10.
Accession Q9P8C9, published Oct. 1, 2000.
Karlsson et al. *Eur J Biochem*. (Dec. 2001) 268:6498-6507.
Bhosale, S.H., Rao, M.B., Deshpande, V.V: Molecular and Industrial Aspects of Glucose Isomerase, *Microbiol Rev.* 60:280-300 (1996).
Meaden, PG, et al., The Xylose Isomerase—Encoding Gene (XylA) of *Clostridium thermosaccharolyticum*: Cloning, Sequencing . . . of XylA Enzymes, *Gene 141*:97-101 (1994).
Herrick, K., Blow, D.M., Carrel H.L.I., Glusker, J.P.: Comparison of Backbone Structures of Glucose Isomerase from *Streptomyces* and *Arthobacter. Protein Engineering 1*:467-469 (1987).
Henrick K et al.: Structures of o-xylose Isomerase from *Arthrobacter* Strain B3728 Containing the Inhibitors Xylitol and D-Sorbitol . . . *J Mol. Biol. 208*:129-157 (1989).
Vangrysperre, W., Van Damme J., Vandekerckhove J., et al., Localization of the Essential Histidine and Carboxylate Group in Xylose Isomerases. *Biochem J. 265*:699-705 (1990).
Bruinenberg P.M., de Bot, P., van Dijken, J., Scheffers, WA.: The Role of Redox Balances on the Anaerobic Fermentation of Xylose by Yeasts. *Eur. J Appl. Microbiol. Biotechnol. 18*:287-292 (1983).
Gardonyi, M. and Hahn-Hagerdal, B.: The *Streptomyces rubiginosus* Xylose Isomerase is Misfolded when Expressed in *Saccharomyces cerevisiae. Enz. Microb. Technol. 32*:252-259 (2003).
Amore R. et al., The Fermentation of Xylose—an Analysis of the Expression of *Bacillus* and *Actinoplanes* Xylose Isomerase Genes in Yeast, *Appl Microbiol. Biotechnol. 30*:351-357 (1989).
Chan, E-C., Ueng, P.P., Chen, L.F.: Metabolism of D-Xylose in *Schizosaccharomyces* Pombe cloned with a Xylose Isomerase Gene, *Appl. Bicrobiol. Biotechnol. 31*: 524-528 (1989).

(Continued)

*Primary Examiner* — Christian Fronda

(74) *Attorney, Agent, or Firm* — Browdy and Neimark, PLLC

(57) ABSTRACT

The present invention relates to host cells transformed with a nucleic acid sequence encoding a eukaryotic xylose isomerase obtainable from an anaerobic fungus. When expressed, the sequence encoding the xylose isomerase confers to the host cell the ability to convert xylose to xylulose which may be further metabolized by the host cell. Thus, the host cell is capable of growth on xylose as carbon source. The host cell preferably is a eukaryotic microorganism such as a yeast or a filamentous fungus. The invention further relates to processes for the production of fermentation products such as ethanol, in which a host cell of the invention uses xylose for growth and for the production of the fermentation product. The invention further relates to nucleic acid sequences encoding eukaryotic xylose isomerases and xylulose kinases as obtainable from anaerobic fungi.

10 Claims, 1 Drawing Sheet

OTHER PUBLICATIONS

UNIPROT Database listing of available xylose isomerase sequences as of Jan. 22, 2002. (*D25 of EPO Oppos*).

Ueng et al., "Molecular cloning of the *Escherichia coli* gene encoding xylose isomerase", *Biotech. Lett.* 7:153-158 (1985). (*D15 in EPO Oppos*).

Chan, E-C. et al., "D-xylose fermentation to ethanol by *Schizosaccharomyces pombe* cloned with xylose isomerase gene", *Biotechnol. Lett.* 8:231-234 (1986). (*D13 in EPO Oppos*).

Walfridsson et al.., "Ethanolic fermentation of xylose with *Saccharomyces cerevisiae* harboring the *Thermus thermophilus xylA* gene, which expresses an active xylose (glucose) isomerase", *Appl. Environ. Microbiol.* 62:4648-4651 (1996). (*D8 in EPO Oppos*).

Kristo et al. *Eur. J. Biochem.* 237:240-246 (1996) (*D23 in EPO Oppos*).

Harhangi et al., "Xylose metabolism in the anaerobic fungus *Piromyces* sp. strain E2 follows the bacterial pathway". *Arch. Microbiol.* 180:134-141 (Jun. 13, 2003) (*D7 in EPO Oppos*).

Madhavan, A. el al., Xylose isomerase from polycentric fungus *Orpinomyces*: gene sequencing, cloning, and expression in *Saccharomyces cerevisiae* for bioconversion of xylose to ethanol. *Appl Microbiol Biotechnol.* 82:1067-78 (Apr. 2009; Epub Dec. 3, 2008).

* cited by examiner

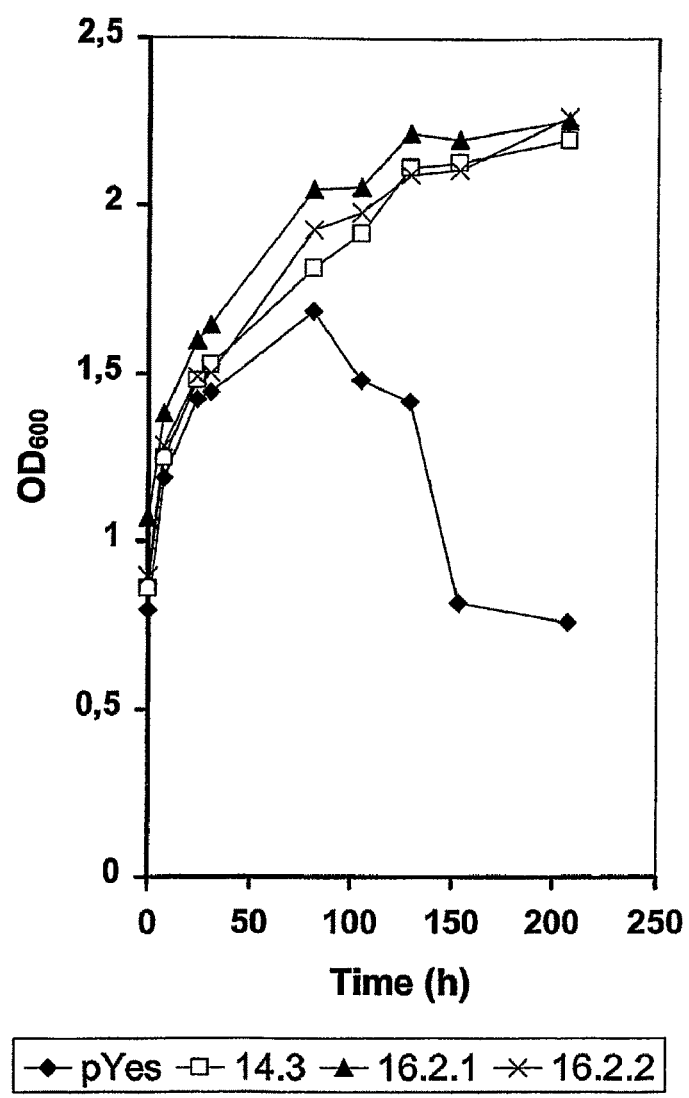

SEQUENCE LISTING

<160> NUMBER OF SEQ ID NOS: 4

<210> SEQ ID NO 1
<211> LENGTH: 437
<212> TYPE: PRT
<213> ORGANISM: Piromyces sp.

<400> SEQUENCE: 1

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
            35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335
```

```
        Thr Asn Phe Asp Ala Lys Thr Arg Arg Asn Ser Thr Asp Leu Glu Asp
                        340                 345                 350

Ile Ile Ile Ala His Val Ser Gly Met Asp Ala Met Ala Arg Ala Leu
                    355                 360                 365

Glu Asn Ala Ala Lys Leu Leu Gln Glu Ser Pro Tyr Thr Lys Met Lys
                370                 375                 380

Lys Glu Arg Tyr Ala Ser Phe Asp Ser Gly Ile Gly Lys Asp Phe Glu
        385                 390                 395                 400

Asp Gly Lys Leu Thr Leu Glu Gln Val Tyr Glu Tyr Gly Lys Lys Asn
                        405                 410                 415

Gly Glu Pro Lys Gln Thr Ser Gly Lys Gln Glu Leu Tyr Glu Ala Ile
                    420                 425                 430

Val Ala Met Tyr Gln
                    435

<210> SEQ ID NO 2
<211> LENGTH: 1669
<212> TYPE: DNA
<213> ORGANISM: Piromyces Sp.

<400> SEQUENCE: 2
gtaaatggct aaggaatatt tcccacaaat tcaaaagatt aagttcgaag gtaaggattc     60
taagaatcca ttagccttcc actactacga tgctgaaaag gaagtcatgg gtaagaaaat    120
gaaggattgg ttacgtttcg ccatggcctg gtggcacact ctttgcgccg aaggtgctga    180
ccaattcggt ggaggtacaa agtctttccc atggaacgaa ggtactgatg ctattgaaat    240
tgccaagcaa aaggttgatg ctggtttcga aatcatgcaa aagcttggta ttccatacta    300
ctgttttcca cgatgttgat ctgtttccga aggtaactct attgaagaat acgaatccaa    360
ccttaaggct gtcgttgctt acctcaagga aaagcaaaag gaaaccggta ttaagcttct    420
ctggagtact gctaacgtct tcggtcacaa gcgttacatg aacggtgcct ccactaaccc    480
agactttgat gttgtcgccc gtgctattgt tcaaattaag aacgccatag acgccggtat    540
tgaacttggt gctgaaaact acgtcttctg gggtggtcgt gaaggttaca tgagtctcct    600
taacactgac caaaagcgtg aaaaggaaca catggccact atgcttacca tggctcgtga    660
ctacgctcgt tccaagggat tcaagggtac tttcctcatt gaaccaaagc caatggaacc    720
aaccaagcac caatacgatg ttgacactga accgctatt ggtttcctta aggcccacaa    780
cttagacaag gacttcaagg tcaacattga agttaaccac gctactcttg ctggtcacac    840
tttcgaacac gaacttgcct gtgctgttga tgctggtatg ctcggttcca ttgatgctaa    900
ccgtggtgac taccaaaacg gttgggatac tgatcaattc ccaattgatc aatacgaact    960
cgtccaagct tggatggaaa tcatccgtgg tggtggtttc gttactggtg gtaccaactt   1020
cgatgccaag actcgtcgta actctactga cctcgaagac atcatcattg cccacgtttc   1080
tggtatggat gctatggctc gtgctcttga aaacgctgcc aagctcctcc aagaatctcc   1140
atacaccaag atgaagaagg aacgttacgc ttccttcgac agtggtattg gtaaggactt   1200
tgaagatggt aagctcaccc tcgaacaagt ttacgaatac ggtaagaaga acggtgaacc   1260
aaagcaaact tctggtaagc aagaactcta cgaagctatt gttgccatgt accaataagt   1320
taatcgtagt taaattggta aaataattgt aaaatcaata aacttgtcaa tcctccaatc   1380
aagtttaaaa gatcctatct ctgtactaat taaatatagt acaaaaaaaa atgtataaac   1440
aaaaaaaagt ctaaaagacg gaagaattta atttagggaa aaaataaaaa taataataaa   1500
caatagataa atccttata ttaggaaaat gtcccattgt attattttca tttctactaa   1560
```

```
aaaagaaagt aaataaaaca caagaggaaa ttttcccttt ttttttttt tgtaataaat    1620 tttatgcaaa tataaatata aataaaataa taaaaaaaa aaaaaaaa                 1669
```

<210> SEQ ID NO 3
<211> LENGTH: 494
<212> TYPE: PRT
<213> ORGANISM: Piromyces sp.

<400> SEQUENCE: 3

```
Met Lys Thr Val Ala Gly Ile Asp Leu Gly Thr Gln Ser Met Lys Val
1               5                   10                  15

Val Ile Tyr Asp Tyr Glu Lys Lys Glu Ile Glu Ser Ala Ser Cys
            20                  25                  30

Pro Met Glu Leu Ile Ser Glu Ser Asp Gly Thr Arg Glu Gln Thr Thr
        35                  40                  45

Glu Trp Phe Asp Lys Gly Leu Glu Val Cys Phe Gly Lys Leu Ser Ala
    50                  55                  60

Asp Asn Lys Lys Thr Ile Glu Ala Ile Gly Ile Ser Gly Gln Leu His
65                  70                  75                  80

Gly Phe Val Pro Leu Asp Ala Asn Gly Lys Ala Leu Tyr Asn Ile Lys
                85                  90                  95

Leu Trp Cys Asp Thr Ala Thr Val Glu Glu Cys Lys Ile Ile Thr Asp
            100                 105                 110

Ala Ala Gly Gly Asp Lys Ala Val Ile Asp Ala Leu Gly Asn Leu Met
        115                 120                 125

Leu Thr Gly Phe Thr Ala Pro Lys Ile Leu Trp Leu Lys Arg Asn Lys
    130                 135                 140

Pro Glu Ala Phe Ala Asn Leu Lys Tyr Ile Met Leu Pro His Asp Tyr
145                 150                 155                 160

Leu Asn Trp Lys Leu Thr Gly Asp Tyr Val Met Glu Tyr Gly Asp Ala
                165                 170                 175

Ser Gly Thr Ala Leu Phe Asp Ser Lys Asn Arg Cys Trp Ser Lys Lys
            180                 185                 190

Ile Cys Asp Ile Ile Asp Pro Lys Leu Leu Asp Leu Leu Pro Lys Leu
        195                 200                 205

Ile Glu Pro Ser Ala Pro Ala Gly Lys Val Asn Asp Glu Ala Ala Lys
    210                 215                 220

Ala Tyr Gly Ile Pro Ala Gly Ile Pro Val Ser Ala Gly Gly Gly Asp
225                 230                 235                 240

Asn Met Met Gly Ala Val Gly Thr Gly Thr Val Ala Asp Gly Phe Leu
                245                 250                 255

Thr Met Ser Met Gly Thr Ser Gly Thr Leu Tyr Gly Tyr Ser Asp Lys
            260                 265                 270

Pro Ile Ser Asp Pro Ala Asn Gly Leu Ser Gly Phe Cys Ser Ser Thr
        275                 280                 285

Gly Gly Trp Leu Pro Leu Leu Cys Thr Met Asn Cys Thr Val Ala Thr
    290                 295                 300

Glu Phe Val Arg Asn Leu Phe Gln Met Asp Ile Lys Glu Leu Asn Val
305                 310                 315                 320

Glu Ala Ala Lys Ser Pro Cys Gly Ser Glu Gly Val Leu Val Ile Pro
                325                 330                 335

Phe Phe Asn Gly Glu Arg Thr Pro Asn Leu Pro Asn Gly Arg Ala Ser
            340                 345                 350

Ile Thr Gly Leu Thr Ser Ala Asn Thr Ser Arg Ala Asn Ile Ala Arg
        355                 360                 365
```

```
Ala Ser Phe Glu Ser Ala Val Phe Ala Met Arg Gly Gly Leu Asp Ala
        370                 375                 380

Phe Arg Lys Leu Gly Phe Gln Pro Lys Glu Ile Arg Leu Ile Gly Gly
385                 390                 395                 400

Gly Ser Lys Ser Asp Leu Trp Arg Gln Ile Ala Asp Ile Met Asn
                405                 410                 415

Leu Pro Ile Arg Val Pro Leu Leu Glu Glu Ala Ala Leu Gly Gly
                420                 425                 430

Ala Val Gln Ala Leu Trp Cys Leu Lys Asn Gln Ser Gly Lys Cys Asp
                435                 440                 445

Ile Val Glu Leu Cys Lys Glu His Ile Lys Ile Asp Glu Ser Lys Asn
            450                 455                 460

Ala Asn Pro Ile Ala Glu Asn Val Ala Val Tyr Asp Lys Ala Tyr Asp
465                 470                 475                 480

Glu Tyr Cys Lys Val Val Asn Thr Leu Ser Pro Leu Tyr Ala
                485                 490

<210> SEQ ID NO 4
<211> LENGTH: 2041
<212> TYPE: DNA
<213> ORGANISM: Piromyces sp.

<400> SEQUENCE: 4
attatataaa ataactttaa ataaaacaat ttttatttgt ttatttaatt attcaaaaaa      60
aattaaagta aaagaaaaat aatacagtag aacaatagta ataatatcaa aatgaagact     120
gttgctggta ttgatcttgg aactcaaagt atgaaagtcg ttatttacga ctatgaaaag     180
aaagaaatta ttgaaagtgc tagctgtcca atggaattga tttccgaaag tgacggtacc     240
cgtgaacaaa ccactgaatg gtttgacaag ggtcttgaag tttgttttgg taagcttagt     300
gctgataaca aaaagactat tgaagctatt ggtatttctg gtcaattaca cggttttgtt     360
cctcttgatg ctaacggtaa ggctttatac aacatcaaac tttggtgtga tactgctacc     420
gttgaagaat gtaagattat cactgatgct gccggtggtg acaaggctgt tattgatgcc     480
cttggtaacc ttatgctcac cggtttcacc gctccaaaga tcctctggct caagcgcaac     540
aagccagaag ctttcgctaa cttaaagtac attatgcttc cacacgatta cttaaactgg     600
aagcttactg gtgattacgt tatggaatac ggtgatgcct ctggtaccgc tctcttcgat     660
tctaagaacc gttgctggtc taagaagatt gcgatatca ttgacccaaa acttttagat     720
ttacttccaa agttaattga accaagcgct ccagctggta aggttaatga tgaagccgct     780
aaggcttacg gtattccagc cggtattcca gtttccgctg gtggtggtga taacatgatg     840
ggtgctgttg gtactggtac tgttgctgat ggtttcctta ccatgtctat gggtacttct     900
ggtactcttt acggttacag tgacaagcca attagtgacc cagctaatgg tttaagtggt     960
ttctgttctt ctactggtgg atggcttcca ttactttgta ctatgaactg tactgttgcc    1020
actgaattcg ttcgtaacct cttccaaatg gatattaagg aacttaatgt tgaagctgcc    1080
aagtctccat gtggtagtga aggtgtttta gttattccat tcttcaatgg tgaaagaact    1140
ccaaacttac aaaccggtcg tgctagtatt actggtctta cttctgctaa caccagccgt    1200
gctaacattg ctcgtgctag tttcgaatcc gccgttttcg ctatgcgtgg tggtttagat    1260
gctttccgta agttaggttt ccaaccaaag gaaattcgtc ttattggtgg tggttctaag    1320
tctgatctct ggagacaaat tgccgctgat atcatgaacc ttccaatcag agttccactt    1380
ttagaagaag ctgctgctct tggtggtgct gttcaagctt tatggtgtct taagaaccaa    1440
```

```
tctggtaagt gtgatattgt tgaactttgc aaagaacaca ttaagattga tgaatctaag    1500
aatgctaacc caattgccga aaatgttgct gtttacgaca aggcttacga tgaatactgc    1560
aaggttgtaa atactctttc tccattatat gcttaaattg ccaatgtaaa aaaaaatata    1620
atgccatata attgccttgt caatacactg ttcatgttca tataatcata ggacattgaa    1680
tttacaaggt ttatacaatt aatatctatt atcatattat tatacagcat ttcattttct    1740
aagattagac gaaacaattc ttggttcctt gcaatataca aaatttacat gaatttttag    1800
aatagtctcg tatttatgcc caataatcag gaaaattacc taatgctgga ttcttgttaa    1860
taaaaacaaa ataaataaat taaataaaca aataaaaatt ataagtaaat ataaatatat    1920
aagtaatata aaaaaaaagt aaataaataa ataaataaat aaaaattttt tgcaaatata    1980
taaataaata aataaaatat aaaaataatt tagcaaataa attaaaaaaa aaaaaaaaaa    2040
a                                                                   2041
```

FERMENTATION OF PENTOSE SUGARS

BACKGROUND OF THE INVENTION

1. Field of the Invention

The present invention relates to host cells transformed with a nucleic acid sequence encoding a eukaryotic xylose isomerase. The xylose isomerase is expressed in the host cell to confer the ability of isomerizing xylose to xylulose. The host cell is used in a process for the production of ethanol and other fermentation products by fermentation of a pentose-containing medium. The present invention further relates to nucleic acid sequences encoding eukaryotic xylose isomerases.

2. Description of the Background Art

Large-scale consumption of the traditional, fossil fuels (petroleum-based fuels) in the last few decades has contributed to high levels of pollution. Moreover, the realization that the world stock of petroleum is not boundless, combined with the growing environmental awareness, has stimulated new initiatives to investigate the feasibility of alternative fuels such as ethanol, which could realize a 60-90% decrease in $CO_2$ production. Although biomass-derived ethanol may be produced by fermentation of hexose sugars that are obtained from many different sources, so far, however, the substrates for industrial scale production or fuel alcohol are cane sugar and corn starch. The drawback of these substrates are the high costs.

Expanding fuel ethanol production requires the ability to use lower-cost feedstocks. Presently, only lignocellulosic feedstock from plant biomass would be available in sufficient quantities to substitute the crops used for ethanol production. The major fermentable sugars from lignocellulosic materials are glucose and xylose, constituting respectively about 40% and 25% of lignocellulose. However, most yeasts that are capable of alcoholic fermentation, like *Saccharomyces cerevisiae*, are not capable of using xylose as a carbon source. Additionally, no organisms are known that can ferment xylose to ethanol with both a high ethanol yield and a high ethanol productivity. To enable the commercial production of ethanol from lignocellulose hydrolysate, an organism possessing both these properties would be required. Thus it is an object of the present invention to provide for a yeast that is capable of both alcoholic fermentation and of using xylose as a carbon source.

D-xylose is metabolically by numerous microorganisms such as enteric bacteria, some yeasts and fungi. In most xylose-utilizing bacteria, xylose is directly isomerized to D-xylulose by xylose (glucose) isomerase (XI). Filamentous fungi and yeasts, are however not capable of this one-step isomerization and first reduce xylose to xylitol by the action of xylose reductase (XR) after which the xylitol is converted to xylulose by xylitol dehydrogenase (XDH). The first step requires NAD(P)H as a co-factor whereas the second step requires $NAD^+$. The xylulose that is produced subsequently enters the pentose phosphate pathway (PPP) after it is phosphorylated by xylulose kinase (XK). Anaerobic fermentation of xylose to ethanol is not possible in organisms with a strictly NADPH dependent xylose reductase (XR). This is because xylitol dehydrogenase (XDH) is strictly $NAD^+$ dependent resulting in a redox imbalance (i.e., $NAD^+$ depletion). To solve the redox imbalance under anaerobic conditions, the organism produces by-products such as glycerol and xylitol. Similarly, aerobic production of β-lactams on xylose is also negatively influenced as compared to β-lactam production on glucose. A likely cause for these low yields again are a relatively high demand of reducing equivalents in the form of NADPH in this route, compared to the use of glucose (van Gulik, W M et al., 2000, *Biotechnol. Bioeng.* 68(6): 602-18.

Over the years many attempts have been made to introduce xylose metabolism in *S. cerevisiae* and similar yeasts, as reviewed in Zaldivar et al, 2001, *Appl. Microbiol. Biotechnol.* 56:17-34). One approach concerns the expression of at least genes encoding a xylose (aldose) reductase and a xylitol dehydrogenase, e.g., the XYL1 and XYL2 of *Pichia stipitis*, in *S. cerevisiae* (U.S. Pat. No. 5,866,382; PCT Publications WO 95/13362 and WO 97/42307). Although this approach enables growth of *S. cerevisiae* on xylose, it generally suffers from a low ethanol productivity and/or yield as well as a high xylitol production, mainly as a result of the redox imbalance between XR and XDH.

The expression of a XI in *S. cerevisiae* or related yeast or in filamentous fungi would circumvent the redox imbalance and consequent xylitol production and excretion. Xylose isomerase genes from several bacteria have been inserted in *S. cerevisiae*, however, expression of mesophilic prokaryotic XIs in *S. cerevisiae* did not lead to active XI (Amore and Hollenberg, 1989, *Nucleic Acids Res.* 17:7515; Amore et al., 1989, *Appl. Microbiol. Biotechnol.* 30:351-357; Chan et al., 1986, *Biotechnol. Lett* 8:231-234; Chan et al., 1989, *Appl. Microbiol. Biotechnol.* 31:524-528; Ho et al., 1983, *Feder. Proc.* 42:2167; Hollenberg, 1987, *EBC-Syniposium on Brewer's Yeast*, Helsinki (Finland), 24-25 Nov. 1986; Sarthy et al., 1987, *Appl. Environ. Microbiol.* 53:1996-2000; Ueng et al., 1985, *Biotechnol. Lett.* 7:153-8). Nevertheless, two XIs from thermophilic bacteria expressed in *S. cerevisiae* showed a specific activity of 1 µmol per minute per mg at 85° C. (Bao et al., 1999, *Weishengwu-Xuebao* 39:49-54; Walfridson et al., 1996, *Appl. Environ. Microbiol.* 61:4184-90). However, at physiological temperature for *S. cerevisiae* (20-35° C.) only a few percent of this activity is left, which is not sufficient for efficient alcoholic fermentation from xylose. Thus, there is still a need for nucleic acids encoding an XI that can be expressed in yeasts to provide sufficient XI activity under physiological conditions to allow for the use of xylose as carbon source.

DESCRIPTION OF THE PREFERRED EMBODIMENTS

Definitions

Xylose Isomerase

The enzyme "xylose isomerase" (EC 5.3.1.5) is herein defined as an enzyme that catalyses the direct isomerization of D-xylose into D-xylulose and vice versa. The enzyme is also known as a D-xylose ketoisomerase. Some xylose isomerases are also capable of catalyzing the conversion between D-glucose and D-fructose and are therefore sometimes referred to as glucose isomerase. Xylose isomerases require magnesium as cofactor. Xylose isomerases of the invention may be further defined by their amino acid sequence as herein described below. Likewise xylose isomerases may be defined by the nucleotide sequences encoding the enzyme as well as by nucleotide sequences hybridizing to a reference nucleotide sequence encoding a xylose isomerase as herein described below.

A unit (U) of xylose isomerase activity is herein defined as the amount of enzyme producing 1 nmol of xylulose per minute, in a reaction mixture containing 50 mM phosphate buffer (pH 7.0), 10 mM xylose and 10 mM $MgCl_2$ at 37° C. Xylulose formed was determined by the method of Dische et al., 1951, *J. Biol. Chem.* 192:583-587) or by HPLC as described in the Examples.

Sequence Identity and Similarity

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (*Computational Molecular Biology*, Lesk, A M, ed., Oxford University Press, New York, 1988; *Biocomputing: Informatics and Genome Projects*, Smith, D W, ed., Academic Press, New York, 1993; *Computer Analysis of Sequence Data, Part I*, Griffin, A M et al., eds., Humana Press, New Jersey, 1994; *Sequence Analysis in Molecular Biology*, von Heine, G., Academic Press, 1987; and *Sequence Analysis Primer*, Gribskov, M et al., eds., M Stockton Press, New York, 1991; and Carillo, H. and Lipman, D., *SIAM J. Applied Math.*, 48:1073, 988.

Preferred methods to determine identity are designed to give the largest match between the sequences tested. Methods to determine identity and similarity are codified in publicly available computer programs. Preferred computer program methods to determine identity and similarity between two sequences include e.g., the GCG program package (Devereux, J., et al., *Nucleic Acids Res* 12(1):387 (1984)), BestFit, BLASTP, BLASTN, and FASTA (Altschul, S F et al., *J. Mol. Biol.* 215:403-10 (1990). The BLAST X program is publicly available from NCBI and other sources (*BLAST Manual*, Altschul, S F, et al., NCBI NLM NIH Bethesda, Md. 20894; Altschul, S F, et al., *J. Mol. Biol.* 215:403-10 (1990). The well-known Smith Waterman algorithm may also be used to determine identity.

Preferred parameters for polypeptide sequence comparison include the following: Algorithm: Needleman and Wunsch, *J. Mol. Biol.* 48:443-53 (1970); Comparison matrix: BLOSSUM62 from Hentikoff et al., *Proc. Natl. Acad. Sci. USA*. 89:10915-19 (1992); Gap Penalty=12; and Gap Length Penalty=4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch (see supra); Comparison matrix: matches=+10, mismatch=0; Gap Penalty=50; Gap Length Penalty=3. (Available as the Gap program from Genetics Computer Group, Madison, Wis.). Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Hybridizing Nucleic Acid Sequences

Nucleotide sequences encoding xylose isomerases or xylulose kinases of the invention may also be defined by their capability to hybridize with the nucleotide sequences of SEQ ID NO:2 or SEQ ID NO:4, respectively, under moderate, or preferably, under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1M salt, or less, preferably 0.2×SSC or any other solution having a comparable ionic strength. Preferably, the hybridization is performed overnight, i.e., at least for 10 hours and, preferably, washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1M salt, preferably 6×SSC or any other solution having a comparable ionic strength, and washing at room temperature in a solution comprising about 1M salt, preferably 6×SSC or any other solution having a comparable ionic strength. Preferably, the hybridization is performed overnight, i.e., at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

Operably Linked

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

Promoter

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

In a first aspect the present invention relates to a transformed host cell that has the ability of isomerizing xylose to xylulose. The ability of isomerizing xylose to xylulose is conferred to the host cell by transformation of the host cell with a nucleic acid construct comprising a nucleotide sequence encoding a xylose isomerase. The transformed host cell's ability to isomerize xylose into xylose is the direct isomerization of xylose to xylulose. This is understood to mean that xylose isomerized into xylulose in a single reaction catalyzed by a xylose isomerase, as opposed to the two step conversion of xylose into xylulose via a xylitol intermediate as catalyzed by xylose reductase and xylitol dehydrogenase, respectively.

The nucleotide sequence encodes a xylose isomerase that is preferably expressed in active form in the transformed host cell. Thus, expression of the nucleotide sequence in the host cell produces a xylose isomerase with a specific activity of at least 10 U xylose isomerase activity per mg protein at 25° C., preferably at least 20, 25, 30, 50, 100, 200 or 300 U per mg at 25° C. The specific activity of the xylose isomerase expressed in the transformed host cell is herein defined as the amount of xylose isomerase activity units per mg protein of cell free lysate of the host cell, e.g., a yeast cell free lysate. Determination of the xylose isomerase activity, amount of protein and preparation of the cell free lysate are as described in Example 1. Alternatively, the specific activity may be determined as indicated in EXAMPLE 4. Accordingly, expression of the nucleotide sequence in the host cell produces a xylose isomerase with a specific activity of at least 50 U xylose isomerase activity per mg protein at 30° C., preferably at least 100, 200, 500, or 750 U per mg at 30° C.

Preferably, expression of the nucleotide sequence in the host cell produces a xylose isomerase with a $K_m$ for xylose that is less than 50, 40, 30 or 25 mM, more preferably, the $K_m$ for xylose is about 20 mM or less.

A nucleotide sequence encoding the xylose isomerase may be selected from the group consisting of:
(a) nucleotide sequences encoding a polypeptide comprising an amino acid sequence that has at least 40, 45, 49, 50, 53, 55, 60, 70, 80, 90, 95, 97, 98, or 99% sequence identity with the amino acid sequence of SEQ ID NO:1;
(b) nucleotide sequences comprising a nucleotide sequence that has at least 40, 50, 55, 56, 57, 60, 70, 80, 90, 95, 97, 98, or 99% sequence identity with the nucleotide sequence of SEQ ID NO:2;
(c) nucleotide sequences the complementary strand of which hybridizes to a nucleic acid molecule sequence of (a) or (b);
(d) nucleotide sequences the sequence of which differs from the sequence of a nucleic acid molecule of (c) due to the degeneracy of the genetic code.

The nucleotide sequence preferably encodes a eukaryotic xylose isomerase, i.e., a xylose isomerase with an amino acid sequence that is identical to that of a xylose isomerase that naturally occurs in an eukaryotic organism. Expression of a eukaryotic xylose isomerase increases the likelihood that the xylose isomerase is expressed in active form in a eukaryotic host cell such as yeast, as opposed to the mesophilic prokaryotic xylose isomerases. More preferably the nucleotide sequence encodes a plant xylose isomerase (e.g., from *Hordeum vulgare*) or a fungal xylose isomerase (e.g., from a *Basidiomycete*). Most preferably, however, the nucleotide sequence encodes a xylose isomerase from an anaerobic fungus, to further increase the likelihood of expression in enzymatically active form in a eukaryotic host cell, particularly in yeast. Most preferred are nucleotide sequences encoding a xylose isomerase from an anaerobic fungus that belongs to the families *Neocallimastix, Caecomyces, Piromyces, Orpinomyces*, or *Ruminomyces*.

A host cell for transformation with a nucleotide sequence encoding a xylose isomerase preferably is a host capable of active or passive xylose transport into the cell. The host cell preferably contains active glycolysis, the pentose phosphate pathway and preferably contains xylulose kinase activity so that the xylulose isomerized from xylose may be metabolized to pyruvate. The host further preferably contains enzymes for conversion of pyruvate to a desired fermentation product such as ethanol, ethylene or lactic acid. A preferred host cell is a host cell that is naturally capable of alcoholic fermentation, preferably, anaerobic alcoholic fermentation. The host cell further preferably has a high tolerance to ethanol and organic acids like lactic acid, acetic acid or formic acid and sugar degradation products such as furfural and hydroxy-methylfurfural. Any of these characteristics or activities of the host cell may be naturally present in the host cell or may be introduced or modified by genetic modification. A suitable host cell is a microorganism like a bacterium or a fungus, however, most suitable as host cell are yeasts or filamentous fungi.

Yeasts are herein defined as eukaryotic microorganisms and include all species of the subdivision *Eumycotina* (Alexopoulos, C J, 1962, In: *Introductory Mycology*, John Wiley & Sons, Inc., New York) that predominantly grow in unicellular form. Yeasts may either grow by budding of a unicellular thallus or may grow by fission of the organism. Preferred yeasts as host cells belong to the genera *Saccharomyces, Kluyveromyces, Candida, Pichia, Schizosaccharomyces, Hansenula, Kloeckera, Schwanniomyces*, and *Yarrowia*. Preferably the yeast is capable of anaerobic fermentation, more preferably anaerobic alcoholic fermentation.

Filamentous fungi are herein defined as eukaryotic microorganisms that include all filamentous forms of the subdivision *Eumycotina*. These fungi are characterized by a vegetative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism of most filamentous fungi is obligately aerobic. Preferred filamentous fungi as host cells belong to the genera *Aspergillus, Trichoderma, Humicola, Acremonium, Fusarium*, and *Penicillium*.

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus, K. fragilis*.

The host cell is transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may, e.g., be based on the yeast 2μ or pKD1 (Fleer et al., 1991, *Biotechnology* 9:968-75) plasmids. Preferably, however, the nucleic acid construct is integrated in one or more copies into the genome of the host cell. Integration into the host cell's genome may occur at random by illegitimate recombination but preferably nucleic acid construct is integrated into the host cell's genome by homologous recombination as is well known in the art of fungal molecular genetics (see e.g., WO 90/14423, EP-A-0 481 008, EP-A-0 635 574 and U.S. Pat. No. 6,265,186).

In a preferred transformed host cell according to the invention, the nucleic acid construct confers to the host cell the ability to grow on xylose as carbon source, preferably as sole carbon source, and preferably under anaerobic conditions, whereby preferably the transformed host produce essentially no xylitol, e.g., the xylitol produced is below the detection limit or, e.g., less than 5, 2, 1% of the carbon consumed on a molar basis. The transformed host cell has the ability to grow on xylose as sole carbon source at a rate of at least 0.01, 0.02, 0.05, 0.1 or 0.2 h$^{-1}$. The transformed host cell of the invention thus expresses a xylose isomerase at a specific activity level defined above.

A host cell may comprises further genetic modifications that result in one or more of the characteristics selected from the group consisting of (a) increase transport of xylose into the host cell; (b) increased xylulose kinase activity; (c) increased flux of the pentose phosphate pathway; (d) decreased sensitivity to catabolite repression; (e) increased tolerance to ethanol, osmolarity or organic acids; and, (f) reduced production of by-products. By-products are understood to mean carbon-containing molecules other than the desired fermentation product and include e.g., xylitol, glycerol and/or acetic acid. Such genetic modifications may be introduced by classical mutagenesis and screening and/or selection for the desired mutant. Alternatively, the genetic modifications may consist of overexpression of endogenous genes and/or expression of a heterologous genes and/or the inactivation of endogenous genes. The genes are preferably chosen form genes encoding a hexose or pentose transporter; a xylulose kinase such as the xylulose kinase genes from *S. cerevisiae* (XKS1 Deng and Ho, 1990, *Appl. Biochem. Biotechnol.* 24-25: 193-9) or *Piromyces* (xylB, i.e., SEQ ID NO:4); an enzyme from the pentose phosphate pathway such as a transaldolase (TAL1) or a transketolase (TKL1) (see, e.g., Meinander et al., 1995, *Pharmacol. Toxicol. Suppl.* 2: 45) glycolytic enzymes, ethanologenic enzymes such as alcohol dehydrogenases. Preferred endogenous genes for inactivation include a hexose kinase gene e.g., the *S. cerevisiae* HXK2 gene (see Diderich et al., 2001, *Appl. Environ. Microbiol.* 67:1587-93); the *S. cerevisiae* MIG1 or MIG2 genes; (unspecific) aldose reductase genes such as the *S. cerevisiae* GRE3 gene (Träff et al., 2001, *Appl. Environ. Microbiol.* 67:5668-74); genes for enzymes involved in glycerol metabolism such as the *S. cerevisiae* glycerol-phosphate dehydrogenase 1 and/or 2 genes; or (hybridizing) homologues of the genes in other host species. Further preferred modifications of host cells for xylose fermentation are reviewed in Zaldivar et al., (2001, supra).

In another aspect the invention relates to a transformed host cell for the production of fermentation products other than ethanol. Such non-ethanolic fermentation products include in principle any bulk or fine chemical that is producible by eukaryotic microorganism such as a yeast or a filamentous fungus. Such fermentation products include, e.g., lactic acid, acetic acid, succinic acid, amino acids, 1,3-propane-diol, ethylene, glycerol, β-lactam antibiotics and cephalosporins.

Transformation of host cells with the nucleic acid constructs of the invention and additional genetic modification of host cells, preferably yeasts, as described above may be carried out by methods well known in the art. Such methods are e.g., known from standard handbooks, such as Sambrook et al. (2001) *Molecular Cloning: A Laboratory Manual* (3$^{rd}$ edition), Cold Spring Harbor Laboratory, Cold Spring Harbor Laboratory Press, or F. Ausubel et al., eds., *Current Protocols in Molecular Biology*, Green Publishing and Wiley Interscience, New York (1987). Methods for transformation and genetic modification of fungal host cells are known from e.g., EP-A-0 635 574, WO 98/46772, WO 99/60102 and WO 00/37671.

In another aspect the invention relates to a nucleic acid construct comprising a nucleotide sequence encoding a xylose isomerase as defined above and used for transformation of a host cell as defined above. In the nucleic acid construct, the nucleotide sequence encoding the xylose isomerase preferably is operably linked to a promoter for control and initiation of transcription of the nucleotide sequence in a host cell as defined below. The promoter preferably is capable of causing sufficient expression of the xylose isomerase in the host cell, to confer to the host cell the ability to isomerize xylose into xylulose. Preferably, the promoter causes a specific xylose isomerase activity in the host cell as defined above. Promoters useful in the nucleic acid constructs of the invention include both constitutive and inducible natural promoters as well as engineered promoters. A preferred promoter for use in the present invention will in addition be insensitive to catabolite (glucose) repression and/or will preferably not require xylose for induction. Promoters having these characteristics are widely available and known to the skilled person. Suitable examples of such promoters include e.g., yeast promoters from glycolytic genes, such as the yeast phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK) promoters; more details about such promoters may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the xylose isomerase is homologous to the host cell in which the xylose isomerase is expressed.

In the nucleic acid construct, the 3'-end of the nucleotide acid sequence encoding the xylose isomerase preferably is operably linked to a transcription terminator sequence. Preferably the terminator sequence is operable in a host cell of choice, such as e.g., the yeast species of choice. In any case the choice of the terminator is not critical, it may e.g., be from any yeast gene, although terminators may sometimes work if from a non-yeast, eukaryotic, gene. The transcription termination sequence further preferably comprises a polyadenylation signal.

Optionally, a selectable marker may be present in the nucleic acid construct. As used herein, the term "marker"

refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g., dihydrofolate reductase, hygromycin-B-phosphotransferase, 3'-O-phosphotransferase II (kanamycin-, neomycin- and G418-resistance). Although the of antibiotic resistance markers may be most convenient for the transformation of polyploid host cells, preferably however, non-antibiotic resistance markers are used, such as auxotrophic markers (URA3, TRP1, LEU2) or the *S. pombe* TPI gene (described by Russell P R, 1985, *Gene* 40:125-130). In a preferred embodiment the host cells transformed with the nucleic acid constructs are marker gene free. Methods for constructing recombinant marker gene free microbial host cells are disclosed in EP-A-0 635 574 and are based oil the use of bidirectional markers such as the *A. nidulans* amdS (acetamidase) gene or the yeast URA3 and LYS2 genes. Alternatively, a screenable marker such as Green Fluorescent Protein, lacZ, luciferase, chloramphenicol acetyltransferase, β-glucuronidase may be incorporated into the nucleic acid constructs of the invention allowing to screen for transformed cells.

Optional further elements that may be present in the nucleic acid constructs of the invention include, but are not limited to, one or more leader sequences, enhancers, integration factors, and/or reporter genes, intron sequences, centromeres, telomeres and/or matrix attachment (MAR) sequences. The nucleic acid constructs of the invention may further comprise a sequence for autonomous replication, such as an ARS sequence. Suitable episomal nucleic acid constructs may, e.g., be based on the yeast 2μ or pKD1 plasmids (Fleer et al., supra). Alternatively the nucleic acid construct may comprise sequences for integration, preferably by homologous recombination. Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook et al., supra, or F. Ausubel et al., 1987, supra.

In another aspect the invention relates to a nucleic acid molecule comprising a nucleotide sequence that encodes a xylose isomerase. The nucleic acid molecule is preferably selected from the group consisting of:
(a) nucleic acid molecules encoding a polypeptide comprising an amino acid sequence that has at least 50, 53, 54, 55, 60, 70, 80, 90, 95, 97, 98, or 99% sequence identity with the amino acid sequence of SEQ ID NO:1;
(b) nucleic acid molecules comprising a nucleotide sequence that has at least 50, 56, 57, 58, 60, 70, 80, 90, 95, 97, 98, or 99% sequence identity with the nucleotide sequence of SEQ ID NO:2;
(c) nucleic acid molecules the complementary strand of which hybridizes to a nucleic acid molecule sequence of (a) or (b);
(d) nucleic acid molecules the sequence of which differs from the sequence of a nucleic acid molecule of (c) due to the degeneracy of the genetic code.

Alternatively, a nucleic acid molecule of (a) may encode a polypeptide comprising an amino acid sequence that has at least 67, 68, 69, 70, 80, 90, 95, 97, 98, or 99% sequence similarity with the amino acid sequence of SEQ ID NO:1. A nucleic acid molecule of (c) preferably hybridizes under moderate conditions, more preferably under stringent conditions as herein defined above. Preferably the nucleic acid molecule is from a eukaryote, more preferably from a eukaryotic microorganism such as a fungus, most preferably from an anaerobic fungus, such as e.g., that anaerobic fungi described above.

Yet another aspect of the invention relates to a nucleic acid molecule comprising a nucleotide sequence that encodes a xylulose kinase, preferably a D-xylulose kinase. A D-xylulose kinase (EC 2.7.1.17; also referred to as a D-xylulokinase) is herein defined as an enzyme that catalyses the conversion of D-xylulose into xylulose-5-phosphate. The nucleic acid molecule is preferably selected from the group consisting of:
(a) nucleic acid molecules encoding a polypeptide comprising an amino acid sequence that has at least 45, 47, 48, 49, 50, 55, 60, 70, 80, 90, 95, 97, 98, or 99% sequence identity with the amino acid sequence of SEQ ID NO:3;
(b) nucleic acid molecules comprising a nucleotide sequence that has at least 30, 37, 38, 39, 40, 50, 60, 70, 80, 90, 95, 97, 98, or 99% sequence identity with the nucleotide sequence of SEQ ID NO:4;
(c) nucleic acid molecules the complementary strand of which hybridizes to a nucleic acid molecule sequence of (a) or (b); and,
(d) nucleic acid molecules the sequence of which differs from the sequence of a nucleic acid molecule of (c) due to the degeneracy of the genetic code.

Alternatively, a nucleic acid molecule of (a) may encode a polypeptide comprising an amino acid sequence that has at least 64, 65, 66, 70, 80, 90, 95, 97, 98, or 99% sequence similarity with the amino acid sequence of SEQ ID NO:3. A nucleic acid molecule of (c) preferably hybridizes under moderate conditions, more preferably under stringent conditions as herein defined above. Preferably the nucleic acid molecule is from a eukaryote, more preferably from a eukaryotic microorganism such as a fungus, most preferably from an anaerobic fungus, such as e.g., that anaerobic fungi described above.

In a further aspect the invention relates to fermentation processes in which the transformed host cells of the invention are used for the fermentation of carbon source comprising a source of xylose, such as xylose. In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g., lignocellulose, xylans, cellulose, starch and the like. For release of xylose or glucose units from such carbohydrates, appropriate carbohydrases (such as xylanases, glucanases, amylases and the like) may be added to the fermentation medium or may be produced by the transformed host cell. In the latter case the transformed host cell may be genetically engineered to produce and excrete such carbohydrases. In a preferred process the transformed host cell ferments both the xylose and glucose, preferably simultaneously in which case preferably a transformed host cell is used which is insensitive to glucose repression to prevent diauxic growth. In addition to a source of xylose (and glucose) as carbon source, the fermentation medium will further comprise the appropriate ingredient required for growth of the transformed host cell. Compositions of fermentation media for growth of microorganisms such as yeasts are well known in the art.

The fermentation process is a process for the production of a fermentation product such as ethanol, lactic acid, acetic acid, succinic acid, amino acids, 1,3-propane-diol, ethylene, glycerol, β-lactam antibiotics such as Penicillin G or Penicillin V and fermentative derivatives thereof and cephalosporins. The fermentation process may be an aerobic or an anaerobic fermentation process. An anaerobic fermentation process is herein defined as a fermentation process run in the absence of oxygen or in which substantially no oxygen is consumed, e.g., less than 5 mmol/L/h, and wherein organic molecules serve as both electron donor and electron acceptors. In the absence of oxygen, NADH produced in glycolysis and biomass formation, cannot be oxidized by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 1,3-propanediol, ethylene, acetic acid or succinic acid.

The fermentation process is preferably run at a temperature that is optimal for the transformed host cell. Thus, for most yeasts or fungal host cells, the fermentation process is performed at a temperature which is less than 38° C. For yeast or filamentous fungal host cells, the fermentation process is preferably performed at a temperature which is lower than 35, 33, 30 or 28° C. and at a temperature which is higher than 20, 22, or 25° C.

A preferred process is a process for the production of ethanol, whereby the process comprises the steps of: (a) fermenting a medium containing a source of xylose with a transformed host cell as defined above, whereby the host cell ferments xylose to ethanol; and optionally, (b) recovery of the ethanol. The fermentation medium may also comprise a source of glucose that is also fermented to ethanol. In the process the volumetric ethanol productivity is preferably at least 0.5, 1.0, 1.5, 2.0, 2.5, 3.0, 5.0 or 10.0 g ethanol per liter per hour. The ethanol yield on xylose and/or glucose in the process preferably is at least 50, 60, 70, 90, 95 or 98%. The ethanol yield is herein defined as a percentage of the theoretical yield, which, for glucose and xylose is 0.51 g. ethanol per g. glucose or xylose.

In a further aspect the invention relates to a process for producing a fermentation product selected from the group consisting of lactic acid, acetic acid, succinic acid, amino acids, 1,3-propane-diol, ethylene, glycerol, β-lactam antibiotics and cephalosporins. The process preferably comprises the steps of (a) fermenting a medium containing a source of xylose with a transformed host cell as defined herein above, whereby the host cell ferments xylose to the fermentation product, and optionally, (b) recovery of the fermentation product. In a preferred process, the medium also contains a source of glucose.

BRIEF DESCRIPTION OF THE DRAWINGS

FIG. 1. Growth curves of *S. cerevisiae* transformant grown on medium containing 25 mM galactose and 100 mM xylose as carbon source. Transformant pYes contains a yeast expression vector without insertion. Transformants 14.3, 16.2.1 and 16.2.2 are transformed with the pYES vector containing the *Piromyces* sp. E2 xylose isomerase coding sequence.

EXAMPLES

Example 1

Cloning of *Piromyces* Xylanase Isomerase and Xylulose Kinase cDNAs

Organism and Growth Conditions

The anaerobic fungus *Piromyces* sp. E2 (ATCC 76762), isolated from feces of an Indian elephant, was grown anaerobically under $N_2/CO_2$ (80%/20%) at 39° C. in medium M2 supplemented with various carbon sources (24). Carbon sources used were Avicel (microcrystalline cellulose type PH 105, Serva, Germany), fructose or xylose (all 0.5%, w/v). After growth ceased, as judged by hydrogen production, the cells were harvested by centrifugation (15,000×g, 4° C., 15 min) or by filtration over nylon gauze (30 μm pore size).

Preparation of Cell-Free Extract

The fungal cells were washed with deionized water to remove medium components. Cell-free extracts were prepared by freezing the cells in liquid nitrogen and subsequent grinding with glass beads (0.10-0.11 mm diameter) in a mortar. Tris/HCl buffer (100 mM, pH 7.0) was added to the powder (1:1, w/v) and after thawing for 15 min the suspension was centrifuged (18,000×g, 4° C., 15 min). The clear supernatant was used as a source of intracellular enzymes.

Enzyme Assays

Xylose isomerase activity was assayed at 37° C. in a reaction mixture containing 50 mM phosphate buffer (pH 7.0), 10 mM xylose, 10 mM $MgCl_2$ and a suitable amount of cell-free extract. The amount of xylulose formed was determined by the cysteine-carbazole method (9). Xylulose kinase and xylose reductase activities were assayed as described by Witteveen, C et al. (28), 1989, *J. Gen. Microbiol.* 135:2163-71. One unit of activity is defined as the amount of enzyme producing 1 nmol of xylulose per min under the assay conditions. Xylulose formed was determined by the method of Dische et al. (supra) or by HPLC using a Biorad HPX-87N column operated at 80° C. and eluted at 0.6 ml/min using 0.01 M $Na_2HPO_4$ as the eluent. Xylose and xylulose were detected by a Refractive Index detector at an internal temperature of 60° C.

Specific activity is expressed as units per mg protein. Protein was determined with the Bio-Rad protein reagent (Bio-Rad Laboratories, Richmond, Calif., USA) with bovine γ-globulin as a standard.

Random Sequencing of a *Piromyees* sp. E2 cDNA Library

The cDNA library constructed in the vector lambda ZAPII as described previously (2) was used. An aliquot of this library was converted to pBluescript SK-clones by mass excision with the ExAssist helper phage (Stratagene, La Jolla, Calif.). Randomly selected clones were sequenced with the M13 reverse primer to obtain 5' part sequences. Incomplete cDNAs were used to synthesize probes which were used to rescreen the library. To obtain full length sequences subclones were generated in pUC18. Sequencing was performed with the ABI prism 310 automated sequencer with the dRhodamine Terminator Cycle Sequencing Ready Reaction DNA Sequencing Kit™ (Perkin-Elmer Applied Biosystems).

Results

Randomly selected clones from a cDNA library of the anaerobic fungus *Piromyces* sp. E2 were sequenced and this resulted in two clones (pH97 and pAK44) which sequences showed high homology to xylose isomerase and D-xyluloki-nase genes, respectively. The clones were analyzed in detail.

Clone pH97 did not contain a complete ORF and therefore the cDNA library was rescreened with a probe designed on the basis of sequence data from clone pH97. This resulted in a clone pR3 with an insert of 1669 bp. An ORF encoding a protein of 437 amino acids with high similarity to xylose isomerases could be identified. Although the 5' untranslated region comprises only 4 bp, the presumed starting methionine residue fitted well into an alignment of known xylose isomerase sequences. The 3' untranslated region was 351 bp long and had a high AT content, which is typical for anaerobic fungi. The ORF contained the amino acids shown to be important for interaction with the substrate (catalytic triad His 102, Asp 105, Asp 340 and Lys 235) and binding of magnesium (Glu 232) (14, 26). Further, the two signature patterns (residues 185-194 and 230-237) developed for xylose isomerases (20) were present. The *Piromyces* sp. E2 xylose isomerase (XylA) shows the highest homology to the enzymes of *Haemophilus influenza* (52% identity, 68% similarity) and *Hordeum vulgare* (49% identity, 67% similarity). The polypeptide deduced from the cDNA sequence corresponds to a molecular mass of 49,395 Da and has a calculated pI of 5.2.

The second clone, pAK44, had an insert of 2041 bp and contained a complete ORF encoding a protein of 494 amino acids with a molecular weight of 53,158 Da and a pI of 5.0. The first methionine is preceded by a 111 bp 5' untranslated region, while the 3' untranslated region comprised 445 bp. Both regions are AT-rich. BLAST and FASTA searches revealed high similarity to xylulokinases. The two phosphate consensus regions defined by Rodriguez-Pena, J M et al. (22) (1998, *FEMS Microbiol Lett* 162:155-160) were found at positions 6-23 and 254-270 as shown in a partial alignment. Moreover the signatures for this family of carbohydrate kinase as described in the Prosite database were identified (131-145 and 351-372). The *Piromyces* sp. E2 xylulokinase (XylB) showed highest homology with the XylB protein of *Haemophilus influenza* (46% identity, 64% similarity).

Example 2

Construction of Yeast Expression Vectors

Expression of Xylose Isomerase from *Piromyces* sp. E2 in *Saccharomyces cerevisiae* cDNA from *Piromyces* sp. E2 was used in a PCR reaction with pfu polymerase (Stratagene). The primers were designed using the sequences from the 5' and 3' ends of the xylose isomerase gene and also contained a Sfi I and a XbaI restriction site. The PCR product was cloned in the pPICZα vector (Invitrogen, Carlsbad, Calif.). To obtain the xylose isomerase gene, the pPICZα vector was digested with EcoRI and XbaI. The digestion product was ligated into the pYes2 vector (Invitrogen). The pYes2 plasmid with the xylose isomerase gene was transformed into *Saccharomyces cerevisiae* (stam BJ1991, gift from Dr. Elizabeth Jones, USA). The genotype of this strain is: matα, leu2, trp1, ura 3-251, prb1-1122 and pep4-3.

Transformants were plated on SC plates (0.67% YNB medium+0.05% L-Leu+0.05% L-Trp+2% glucose+2% agarose). Untransformed cells can not grow on these plates.

Induction

Transformed *Saccharomyces cerevisiae* cells were grown on glucose medium at 25° C. for 72 h (raffinose can be used as an alternative for glucose). Cells were harvested and resuspended in SC medium with galactose instead of glucose. After 8 h of induction cells were harvested and lysed using glass beads (0.10-0.11 mm diameter) and "breaking buffer" (50 mM phosphate buffer+5% glycerol+protease inhibitor). After lysis the mixture was centrifuged (18,000×g, 4° C., 15 min). The clear supernatant was used to determine xylose isomerase activity using the method described above (Example 1). An activity of 10 U per mg protein was measured at 37° C.

Example 3

Growth of Transformed Yeast Strains on Xylose

Medium Composition

*Saccharomyces cerevisiae* strains were grown on SC-medium with the following composition: 0.67% (w/v) yeast nitrogen base; 0.01% (w/v) L-tryptophan; 0.01% (w/v) L-leucine and either glucose, galactose or xylose, or a combination of these substrates (see below). For agar plates the medium was supplemented with 2% (w/v) bacteriological agar.

Growth Experiment

*Saccharomyces cerevisiae* strain BJ1991 (genotype: matα, leu2, trp1, ura 3-251, prb1-1122, pep4-3) transformed with pYes2 without insertion and three selected transformants (16.2.1; 16.2.2 and 14.3) containing pYes2 with the *Piromyces* sp. E2 xylose isomerase gene were grown on SC-agar plates with 10 mM glucose as carbon source. When colonies were visible, single colonies were used to inoculate liquid SVC-medium with 100 mM xylose and 25 mM galactose as carbon sources. Growth was monitored by measuring the increase in optical density at 600 nm on a LKB Ultrospec K spectrophotometer.

Results

The results of the growth experiments are compiled in FIG. 1. The culture with the BJ1991 strain transformed with pYes2 without insertion shows an increase in $OD_{600}$ up to 80 h. After this time a gradual decrease is observed. This is caused by aggregation of the yeast cells which is often observed at the end of growth. The cultures with the three transformants do not stop growing after 80 h and show a further increase up to at least 150 h.

Example 4

Construction of a New, Improved, Yeast Expression Vector for Constitutive Expression of the *Piromyces* sp. E2 Xylose Isomerase in *Saccharomyces cerevisiae*

The pPICZα vector, containing the *Piromyces* sp. E2 gene coding for xylose isomerase, was used as a template for PCR with $Vent_R$ DNA polymerase (New England Biolabs). The primers were designed using the 5' and 3' sequences of the gene coding for xylose isomerase and included an EcoRI and an SpeI site. Additionally the primers were designed to remove the XbaI site found in the pPICZα construct, replacing it with a stop codon (TAA). The final product was designed to restore the original open reading frame, without the added amino acids (His and c-Myc tags) found in the pPICZα construct. The PCR product was cut with EcoRI and SpeI. The final product was cloned into a vector derived from pYES2 (Invitrogen). In this vector the GAL1 promoter found in pYES2 was replaced by the TPI1 promoter in order to ensure constitutive expression of the xylose isomerase, thereby eliminating the need for galactose in the medium. The TPI1 promoter was cloned from a modified form of plasmid pYX012 (R&D systems). The promoter was cut out as a NheI-EcoRI fragment.

Both the TPI1 promoter and the PCR product of the gene coding for the xylose isomerase were ligated into pYES2 cut with SpeI and XbaI. This plasmid was used to transform *Saccharomyces cerevisiae* strain CEN.PK113-5D (gift from Peter Kötter, Frankfurt). The genotype of the strain is: MatA ura3-52. Transformants were selected on mineral medium plates (Verduyn et al, "Effect of benzoic acid on metabolic fluxes in yeasts: a continuous-culture study on the regulation of respiration and alcoholic fermentation" (1992) *Yeast* 8(7): 501-17) with 2% glucose as the carbon source. Untransformed cells cannot grow on these plates.

Transformants were grown on glucose/xylose mixtures in carbon-limited chemostat cultures. Transformants grown under these conditions exhibit high xylose isomerase activities (800 units per mg at 30° C.) according to a specific enzyme assay as developed by Kersters-Hildersson et al, "Kinetic characterization of D-xylose isomerases by enzymatic assays using D-sorbitol dehydrogenase." 1987, *Enz. Microb. Technol.* 9:145-48). The in vitro activity of xylose isomerase in the cell-free extracts of the transformed *S. cerevisiae* strain was dependent on bivalent cations ($Mg^{2+}$ or $Co^{2+}$) and a relatively low Km value for xylose of approximately 20 mM was measured.

What is claimed is:

1. A process for producing ethanol, comprising the steps of:
   (a) fermenting medium containing a source of xylose with a cultured yeast cell that
      (i) is transformed with a nucleic acid expression construct comprising a nucleotide sequence that encodes xylose isomerase protein, the amino acid sequence of which is at least 90% identical with SEQ ID NO:1, to which is operatively linked
      (ii) a promoter that drives active expression of the xylose isomerase coding sequence in the transformed cell,
      wherein the expression construct is expressible in said cell, and expression thereof confers on the cell the ability to directly isomerize xylose to xylulose, and thereby, to produce ethanol; and
   (b) optionally, recovering the ethanol from said medium.

2. The process according to claim 1, wherein the medium also contains a source of glucose.

3. The process according to claim 1, wherein the production of ethanol occurs at a rate of at least 0.5 g ethanol per liter per hour.

4. The process according to claim 1, wherein the ethanol yield is at least 50%.

5. A process for producing a non-ethanolic fermentation product, which process comprises the steps of:
   (a) fermenting a medium containing a source of xylose with a cultured yeast cell that:
      (i) is transformed with a nucleic acid expression construct comprising a nucleotide sequence that encodes xylose isomerase protein, the amino acid sequence of which is at least 90% identical with SEQ ID NO:1, which nucleotide sequence is operatively linked to a promoter that drives active expression of the xylose isomerase coding sequence in the transformed cell,
      (ii) expresses one or more enzymes that confers on the cell the ability to produce a non-ethanolic fermentation product,
      wherein, expression of the construct confers on the cell the ability to directly ferment and isomerize xylose to xylulose and thereby produce said non-ethanolic fermentation product; and
   (b) optionally, recovering the non-ethanolic fermentation product from said medium.

6. The process of claim 5 wherein the fermentation product is selected from the group consisting of lactic acid, acetic acid, succinic acid, an amino acid, 1,3-propanediol, ethylene, and glycerol.

7. A process according to claim 5, wherein the medium also contains a source of glucose.

8. The process of claim 5, wherein the cell further comprises a genetic modification that results in decreased alcohol dehydrogenase activity so as to reduce ethanol production by said cell.

9. The process according to claim 1 wherein the xylose isomerase amino acid sequence that is encoded by said coding nucleotide sequence:
   (A) comprises a first xylose isomerase signature pattern defined by the presence of residues 185-194 of SEQ ID NO:1;
   (B) comprises a second xylose isomerase signature pattern defined by the presence of residues 230-237 of SEQ ID NO:1;
   (C) comprises a catalytic triad including the following four residues at the indicated positions in SEQ ID NO:1: His 102 plus Asp 105, and Asp 340 and Lys 235; and,
   (D) comprises a Mg-binding site that is residue Glu 233 of SEQ ID NO:1.

10. The process according to claim 5 wherein the xylose isomerase amino acid sequence that is encoded by said coding nucleotide sequence:
   (A) comprises a first xylose isomerase signature pattern defined by the presence of residues 185-194 of SEQ ID NO:1;
   (B) comprises a second xylose isomerase signature pattern defined by the presence of residues 230-237 of SEQ ID NO:1;
   (C) comprises a catalytic triad including the following four residues at the indicated positions in SEQ ID NO:1: His 102 plus Asp 105, and Asp 340 and Lys 235; and,
   (D) comprises a Mg-binding site that is residue Glu 233 of SEQ ID NO:1.

* * * * *